United States Patent [19]

Jöensson et al.

[11] 4,218,472
[45] Aug. 19, 1980

[54] GEMINALLY DISUBSTITUTED INDENE DERIVATIVES

[75] Inventors: Åake N. Jöensson, Solna; Tomas G. Kempe, Enebyberg; Lembit Mikiver, Jaerna; Bengt Å. Sparf, Traangsund, all of Sweden

[73] Assignee: AB Kabi, Stockholm, Sweden

[21] Appl. No.: 930,073

[22] Filed: Aug. 1, 1978

[30] Foreign Application Priority Data

Aug. 5, 1977 [GB] United Kingdom ............... 32947/77

[51] Int. Cl.² .......................... A01N 9/20; A01N 9/22; C07C 91/22
[52] U.S. Cl. ............................... 424/316; 260/326 R; 260/326 D; 260/326.5 C; 260/348.44; 260/348.52; 260/349; 260/501.15; 260/501.18; 260/559 D; 260/562 B; 260/566 F; 260/567.6 M; 260/570.5 C; 260/570.6; 260/570.8 R; 260/570.8 TC; 260/649 R; 424/267; 424/274; 424/329; 424/330 D; 546/15; 546/203; 560/19; 568/322; 568/327
[58] Field of Search ................. 260/501.18, 570.6; 424/316, 330

[56] References Cited

U.S. PATENT DOCUMENTS

| | | | |
|---|---|---|---|
| 2,532,292 | 12/1950 | Cusic | 260/570 UX |
| 2,914,561 | 11/1959 | Allen et al. | 260/570 |
| 2,971,001 | 2/1961 | Palopoli et al. | 260/570 X |
| 2,987,442 | 6/1961 | McLean et al. | 260/570.7 X |
| 3,205,136 | 9/1965 | Tedeschi | 260/570 X |
| 3,255,249 | 6/1966 | Howe et al. | 260/570.6 X |
| 3,463,808 | 8/1969 | Bond et al. | 260/570.6 X |
| 3,641,153 | 2/1972 | Kyburz et al. | 260/570.6 X |
| 4,001,330 | 1/1977 | Curran | 260/570.6 |
| 4,127,675 | 11/1978 | Murakami et al. | 260/570.7 X |
| 4,136,116 | 1/1979 | Kyburz et al. | 260/570.6 X |

*Primary Examiner*—Robert V. Hines
*Attorney, Agent, or Firm*—Pollock, Vande Sande & Priddy

[57] ABSTRACT

New geminally disubstituted indenes are of general formula I

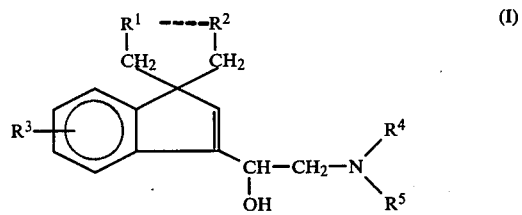

wherein each of $R^1$ and $R^2$ is hydrogen or $R^1$ and $R^2$ together form a direct bond or an alkylene group $-(CH_2)_n-$, in which n is an integer from 1 to 4, $R^3$ is hydrogen, $C_{1-3}$-alkoxy or halogen, and each of $R^4$ and $R^5$ is hydrogen or $C_{1-4}$-lower alkyl, or $R^4$ and $R^5$ together form an alkylene group $-(CH_2)_m-$, in which m is an integer from 3 to 6; and the corresponding amine oxides, quaternary ammonium compounds and salts with physiologically acceptable acids.

The indenes find use in treating incontinence, as a mucous membrane decongestant, as a blood pressure reducing agent, as vasocostrictor or as an anti-reserpine agent.

The indenes may be prepared by processes known per se involving (a) synthesing the side chain $-CH(OH)CH_2NR^4R^5$ by a method known per se in an indenyl precursor of a formula I compound in which the side chain is incomplete or (b) introducing the double bond into an indanyl precursor of a formula I compound in which the double bond is absent or (c) releasing the terminal amino group in a precursor of a formula I compound in which the terminal amino group is protected.

38 Claims, No Drawings

GEMINALLY DISUBSTITUTED INDENE DERIVATIVES

FIELD OF THE INVENTION

This invention relates to new geminally disubstituted indenes, to methods for their preparation, to pharmaceutical compositions containing them and to their use in therapy.

DETAILED DESCRIPTION OF THE INVENTION

The present invention provides geminally disubstituted indenes characterised in that they are of the general formula (I)

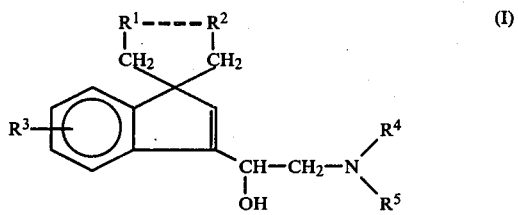

(I)

wherein each of $R^1$ and $R^2$ is hydrogen or $R^1$ and $R^2$ together form a direct bond or an alkylene group —$(CH_2)_n$—, in which n is an integer from 1 to 4, $R^3$ is hydrogen, $C_{1-3}$-alkoxy or halogen, and each of $R^4$ and $R^5$ is hydrogen or $C_{1-4}$-lower alkyl, or $R^4$ and $R^5$ together form an alkylene group —$(CH_2)_m$—, in which m is an integer from 3 to 6; and the corresponding amine oxides, quaternary ammonium compounds and salts with physiologically acceptable acids.

The compounds of formula (I) contain an asymmetric carbon atom, and the invention includes racemic and other mixtures of the optical isomers as well as the optically active isomers themselves. The more active isomer can be separated in conventional manner e.g. by fractional crystallization of diastereoisomeric salts.

In the compounds of the invention prepared compounds are those in which $R^1$ and $R^2$ are each H or those where $R^1$ and $R^2$ together represent —$CH_2$— or —$CH_2$—$CH_2$—, those where $R^3$ is H and those where $R^4$ is H and $R^5$ is H or $CH_3$.

When $R^3$ is alkoxy or halogen, the substituent may be for example, methoxy or ethoxy or chloro or bromo, particularly at the 5-position on the indene ring.

The compounds of the invention may be presented in free base form or as amino oxides, quaternary ammonium compounds or salts with pharmaceutically acceptable acids. The acid may be inorganic e.g. hydrochloric, sulphuric or phosphoric acid or organic e.g. acetic, oxalic, fumaric or tartaric acids. Quaternary ammonium compounds of interest include those which are triorgano ammonium halides or sulphates e.g. triethylammonium chlorides. Unless the context requires otherwise, references in this specification to the compounds of the invention includes a reference to their amine oxides, quaternary ammonium salts and salts with pharmaceutically acceptable acids.

The new compounds according to the invention exhibit interesting pharmacodynamical properties, indicating their utility as drugs. In particular, the compounds present a pronounced sympatomimetic effect, illustrated by the effect on rat vas deferens, a screening test for noradrenaline like activity. Tests on isolated urethra strips of cat have shown that a representative example of the compounds of the invention is considerably more active on this organ than noradrenaline, while at the same time exhibiting a clearly reduced hypertensive effect on anaesthetized cat compared to noradrenaline. The selective effect on urethra has also been illustrated by similar tests on aortic strips of rabbit.

These and other properties make the compounds of the invention useful as drugs against stress incontinence in women, and the compounds are also of interest as mucous membrane decongestants, as blood pressure reducing agents, and as vasoconstrictors (together with local anaesthetics). Some of the compounds also have anti-reserpine effect.

Various methods are available for the preparation of the compounds of formula I and normally involve (a) synthesising the side chain —$CH(OH)CH_2NR^4R^5$ by a method known per se in an indenyl precursor of a formula I compound in which the side chain is incomplete or (b) introducing the double bond into an indenyl precursor of a formula I compound in which the double bond is absent or (c) releasing the terminal amino group in a precursor of a formula I compound in which the terminal amino group is protected.

More specifically, the formula I compounds can be prepared by one of the synthesis described below in which the symbol "Ring" denotes the ring system.

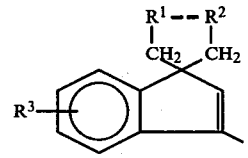

where $R^1$, $R^2$ and $R^3$ are as defined above.

(a) Reacting a compound of the general formula (II)

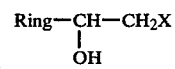

(II)

where X is a reactive leaving group, with an amine (III)

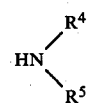

(III)

Preferred leaving groups are halogen or esterified hydroxyl groups such as arylsulphonic ester groups e.g. as tosyl and phosphonic ester groups.

This reaction (a) can also be carried out using a protected amine instead of the amine (III), in which case the amino protecting group is removed after the reaction. Suitable protected amines are carbamic esters (such as $HN(R^6)COOAlkyl$) and imides, such as succinimide, phthalimide, and the like.

(b) Reducing a compound of the general formula (IV)

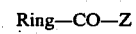

(IV)

wherein Z is an aminomethyl group

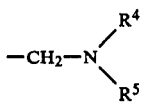

or a group that can be reduced to this aminomethyl group under conditions under which the —CO— group is reduced to the

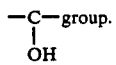

This reduction can also be carried out when the amino group is blocked by an amino protecting group, which is removed after the reduction.

Preferred reducing agents are complex metal hydrides such as sodium borohydride and lithium aluminium hydride, and the reaction is preferably carried out in an inert solvent.

Examples of suitable groups Z, which can be reduced to the aminomethyl group —$CH_2NR^4,R^5$ under the reduction conditions, are carbamic ester derivatives such as —$CH_2NR^6$, COOAlkyl (which are reduced to amines —$CH_2NR^6$, $CH_3$), dicarboxylic acidamidomethyl derivatives

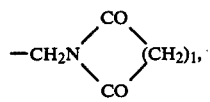

wherein l is an integer from 2 to 4 (which are reduced to tert.amines —$CH_2$—$N(CH_2)_{l+2}$), amide groups such as —CO—$NR^4R^5$ (in which the —CO—group is reduced to —$CH_2$—), azidomethyl groups such as —$CH_2$—$N_3$ (which are reduced to —$CH_2$—$NH_2$), diazomethyl groups such as —$CHN_2$ (which are reduced to —$CH_2NH_2$), and nitromethyl groups —$CH_2NO_2$ (which are reduced to —$CH_2NH_2$).

(c) Reducing a compound of the formula (V)

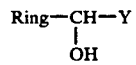

wherein Y is a group which can be converted to the aminomethyl group —$CH_2NR^4,R^5$ by reduction. Examples of suitable groups Y are amide groups (—CO—$NR^4,R^5$), a cyano group (—CN), an azidomethyl group (—$CH_2N_3$), iminomethyl groups (—CH=$NR^6$), an oximinomethyl group (—CH=NOH), hydrazonomethyl groups (—CH=N—$NH_2$, which may be substituted with e.g. alkyl), the nitromethyl group (—$CH_2$—$NO_2$), and the like.

This reaction can also be carried out by reducing a compound of formula (V), in which the hydroxyl group is protected e.g. by esterification or silylation. The hydroxy protecting group is removed either during the reduction or afterwards, e.g. by hydrolysis.

The reductions according to syntheses (b) and (c) can be carried out by using a great variety of reducing agents and reaction conditions, it being well within the competence of chemists experienced in organic synthesis to choose suitable reducing agents and conditions depending on the nature of the groups to be reduced. The reduction can, for example, be carried out by using a complex metal hydride such as sodium borohydride or lithium aluminiumhydride in an inert solvent. Alternatively, catalytically activated hydrogen can be used, the reaction being carried out in an inert solvent and in the presence of a catalyst such as a platinum, a palladium or a nickel catalyst.

(d) Oxidizing a compound of the formula (VI)

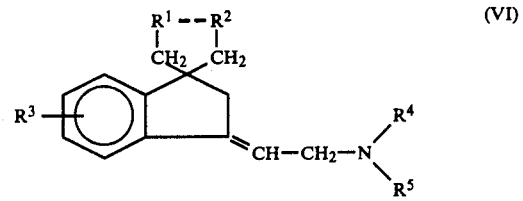

to form a compound of formula (VII) or (VIII)

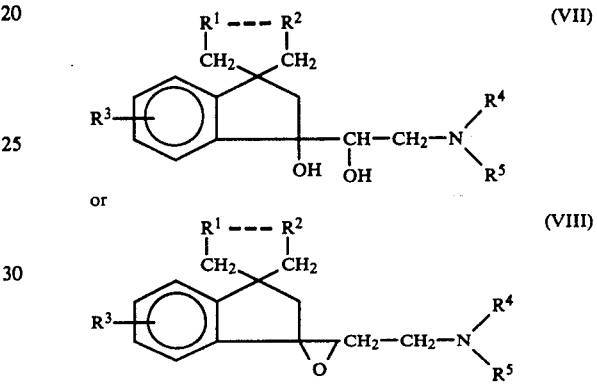

which is then converted into a compound of formula (I) by dehydration or rearrangement (heating or treatment with a catalysing acid).

This reaction can also be carried out using a compound corresponding to formula (VI), in which the amino group is protected, acyl groups being suitable amino protecting groups. In this case the amino protecting group is removed after the reaction.

Preferred oxidizing agents are peroxy acids such as peracetic acid, perbenzoic acid or chloroperbenzoic acid, permanganates, osmium tetroxide, and the like.

(e) Reacting an epoxide of formula (IX)

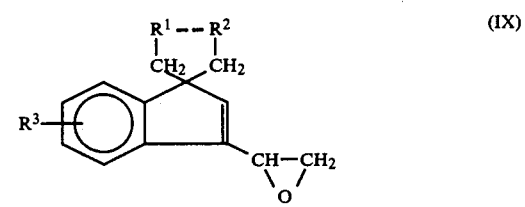

with an amine of formula (III)

(f) Removing the amino protecting group from a compound of formula (X)

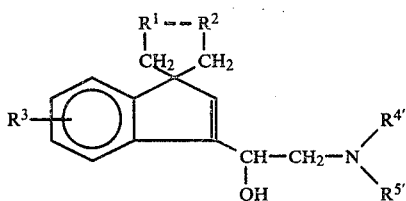

(X)

wherein $R^{4'}$ and $R^{5'}$ have the same meaning as $R^4$ and $R^5$ or signify an amino protecting group, at least one of $R^{4'}$ and $R^{5'}$ being such as amino protecting group.

A great variety of amino protecting groups are available to chemists experienced in organic synthesis. These groups can, for example, be split off by hydrolysis (acid or alkaline), by hydrogenation, by hydrazinolysis, etc., depending on the nature of the group.

Primary and secondary amines of formula (I) can be converted into the corresponding secondary or tertiary amines by alkylation, e.g. by treatment with an alkylating agent such as an alkyl halide. Tertiary amines can similarly be converted into the corresponding quaternary ammonium compounds, especially lower alkyl ammonium compounds. The alkylation can also be carried out by acylation of the primary or secondary amine, whereupon the acyl group is reduced to the corresponding alkyl group in analogy with method (b) above.

The amines of formula (I) can, if desired, be converted into the corresponding salts with physiologically acceptable acids, and tertiary amines of formula (I) can be converted into the corresponding amine oxides by treatment with a suitable oxidation agent, for example a peroxide such as hydrogen peroxide. Tertiary amines of formula (I) can be dealkylated to the corresponding secondary amines, for example as described in the following Examples.

Where the starting materials necessary for preparing the compounds according to the invention by the above described methods are not previously reported in the literature or described in the following Examples, they can be prepared by methods analogous to those used to prepare known starting materials and/or in analogy with the following Examples.

The compounds of the invention can be formulated into pharmaceutical compositions together with pharmaceutically acceptable carriers, and the invention includes such compositions, which may be in the form of e.g. tablets or solutions, preferably in unit dose form. The invention also comprises the use of the compounds of the invention in treating stress incontinence, as mucous membrane decongestants, as blood pressure reducing agents, as vasoconstrictors and as anti-reserpine agents and methods of treating the above mentioned conditions by administering a therapeutically effective amount of a compound of formula (I) to a host in need of such treatment. The required dosage varies depending on the needs and requirements in the specific situation and on the specific substance used. For adults, a daily dosage of 0.1 mg to 100 mg is usually sufficient.

The invention is further illustrated in the following Examples.

EXAMPLE 1

3-Bromo-1,1-dialkylindenes (starting materials)

The 1,1-dialkylindene (1 mole) in dichloromethane (100 ml) is treated dropwise with stirring at 5° C. with a solution of bromine (1 mole) in dichloromethane (500 ml). After stirring for an additional 30 minutes, the solvent is evaporated under reduced pressure and the crude 2,3-dibromo-1,1-dialkylindene is dissolved in tetrahydrofuran (1100 ml) and treated at −20° C. with potassium tert.-butoxide (112 g). After completed addition, the mixture is allowed to come to about 20° C., diluted with water (3 liters) and extracted with diethyl ether (3×400 ml). The ether solution is washed with water and dried with sodium sulphate. Evaporation of the ether and distillation of the remaining oil gives the desired 3-bromo-1,1-dialkylindene as an oil of fairly low stability which are immediately used for the subsequent steps. The following compounds were prepared:

3'-Bromospiro(cyclopentane-1,1'-indene), b.p. 120° C./0.5 torr.

3'-Bromo-5'-methoxyspiro(cyclopentane-1,1'-indene), b.p. 130°–132° C./0.1 torr.

3-Bromo-1,1-dimethylindene, unstable oil which is used without distillation.

3'-Bromospiro(cyclohexane-1,1'-indene), unstable oil which is used without distillation.

3'Bromospiro(cyclopropane-1,1'-indene), b.p. 127°–128° C./0.5 torr.

EXAMPLE 2

2-Dimethylamino-1-[spiro(cyclopentane-1,1'-indene)-3'-yl]ethanol (a) 1-[spiro(cyclopentane-1,1'-indene)-3'-yl]ethanol 3'-Bromospiro(cyclopentane-1,1'-indene) (23 g) is dissolved in tetrahydrofuran (200 ml) and cooled to −70° C. While stirring under nitrogen, n-butyllithium (75 ml of a 2 M solution in hexane) is added followed after 30 minutes by acetaldehyde (14 g) in one portion. Stirring and cooling is maintained for 30 minutes whereupon the mixture is allowed to come to about 20° C. and is kept there for 2 hours. Water (600 ml) is then added and the solution is extracted three times with diethyl ether. The ether extracts are washed, dried over sodium sulphate and the ether is distilled off. Distillation of the residual oil gives the title alcohol, b.p. 139° C./0.4 torr.

(b) 3'-Acetylspiro(cyclopentane-1,1'-indene)

The alcohol from step (a) (14.3 g) is stirred for 2 days at about 20° C. with manganese dioxide (150 g) in light petroleum ether (b.p. 40°–60° C.; 450 ml). Solid material is filtered off and the filtrate concentrated. Distillation of the residual oil gives the title ketone, b.p. 148°–150° C./0.5 torr.

(c) 3'-(α-Bromoacetyl)spiro(cyclopentane-1,1'-indene)

Pyrrolidone hydrotribromide [(pyrrolidone)$_3$HBr$_3$] is added at about 20° C. to the ketone from step (b) (12 g) in tetrahydrofuran (1500 ml) containing 10 drops of concentrated sulphuric acid. The mixture is stirred for 24 hours. Precipitated salts are removed by filtration and the filtrate is concentrated to a small volume. Water (200 ml) is added and the mixture is extracted three times with diethyl ether. After drying the solvent is evaporated, yielding a semi-crystalline residue. Crystallization from methanol gives the pure bromoacetyl title compound, m.p. 75°–77° C.

(d)
N,N-dimethyl-2-oxo-2-[spiro(cyclopentane-1,1'-indene)-3'-yl]ethylamine

The bromoacetyl compound from step (c) (7.0 g) is added to a solution of dimethylamine (19 g) in methanol (100 ml) and kept for 2 hours. After concentration of the solution, the residual oily material is treated with water and diethyl ether. The ether extract is washed and dried. Evaporation of the solvent gives the title ketoamine as a colourless oil. A sample in diethyl ether is treated with oxalic acid, giving the crystalline hydrogen oxalate, m.p. 215° C.

(e)
2-Dimethylamino-1-[spiro(cyclopentane-1,1'-indene)-3'-yl]ethanol

The crude amino ketone from step (d) (2.0 g) in ethanol (50 ml) is treated for 2 hours at about 20° C. with sodium borohydride (2.0 g). Water is added and the amine is extracted into diethyl ether. The ether solution is dried, concentrated to about 100 ml, and then added to a solution of oxalic acid (1.5 g) in ether (500 ml). The precipitated salt is collected and crystallized from acetonitrile. M.p. 133°–134° C.

The following compounds were prepared by the procedure described in steps (d) and (e) above, using the corresponding amines:
2-tert.-Butylamino-1-[spirocyclopentane-1,1'-indene)-3'-yl]-ethanol (the reaction between tert.-butylamine and bromo-ketone is carried out at 120° C. for 2 days). Hydrochloride, m.p. 292° C.
2-Pyrrolidino-1-[spiro(cyclopentane-1,1'-indene)-3'-yl]ethanol, hydrogen oxalate, m.p. 167° C.
2-Piperidino-1-[spiro(cyclopentane-1,1'-indene)-3'-yl]ethanol, hydrogen oxalate, m.p. 179.5° C.

EXAMPLE 3

2-Dimethylamino-1-[spiro(cyclopentane-1,1'-indene)-3'-yl]ethanol

3'-Bromoacetylspiro(cyclopentane-1,1'-indene) (7.5 g) in ethanol (150 ml) is stirred at about 20° C. with sodium borohydride (3.0 g) for 15 minutes. The solution is diluted with water and extracted three times with diethyl ether. The extracts are dried and the solvent removed, giving crude 2-bromo-1-[spiro(cyclopentane-1,1'-indene)-3'-yl]ethanol. This bromohydrine is dissolved in dioxane (75 ml) and dimethylamine (10 g) is added. The solution is heated in an autoclave at 90° C. for 2 hours. Evaporation of excess of dimethylamine and solvent gives an oily residue, which is treated with 2 N sodium hydroxide solution. Extraction with dichloromethane, drying of the extract and evaporation of the solvent gives the title amine as a colourless oil, which on treatment with oxalic acid in acetonitrile solution is converted to the crystalline hydrogen oxalate; m.p. 133°–134° C. after crystallization from acetonitrile.

The following compounds were prepared in an analogous manner, using the corresponding amines:
2-Pyrrolidino-1-[spiro(cyclopentane-1,1'-indene)-3'-yl]ethanol, hydrogen oxalate, m.p. 167° C.
2-Methylamino-1-[spiro(cyclopentane-1,1'-indene)-3'-yl]ethanol, free base, m.p. 134° C.
2-Piperidino-1-[spiro(cyclopentane-1,1'-indene)-3'-yl]ethanol, hydrogen oxalate, m.p. 179.5° C.
2-Ethylamino-1-[spiro(cyclopentane-1,1'-indene-3'-yl]ethanol, hydrochloride, m.p. 227° C.

EXAMPLE 4

2-Amino-1-[spiro(cyclopentane-1,1'-indene)-3'-yl]ethanol

Crude 2-bromo-1-[spiro(cyclopentane-1,1'-indene)-3'-yl]ethanol (7.3 g; prepared as described in Example 3) in dimethylformamide (100 g) is stirred at 40° C. for 4 hours with potassium phthalimide (5.0 g), then diluted with water and extracted three times with chloroform. The combined extracts are dried and evaporated to dryness. The crude 2-phthalimido-1-[spiro(cyclopentane-1,1'-indene)-3'-yl]ethanol is added to ethanol (100 ml) containing hydrazine hydrate (1.5 g). The reaction mixture is stirred under reflux for 4 hours, concentrated hydrochloric acid (2 ml) is added, and the mixture is heated for 15 minutes. The solution is cooled, filtered from the solid precipitate and concentrated to a small volume. The concentrate is made alkaline with 2 N sodium hydroxide solution and repeatedly extracted with diethyl ether. Evaporation of the ether and crystallization of the residual product from cyclohexane gives 2-amino-1-[spiro(cyclopentane-1,1'-indene)-3'-yl]ethanol, m.p. 76°–78° C.

EXAMPLE 5

2-Pyrrolidino-1-[spiro)cyclopentane-1,1'-indene)-3'-yl]ethanol

3'-Bromoacetylspiro(cyclopentane-1,1'-indene) (5.8 g) in dimethylformamide (50 ml) is stirred at 40° C. for 4 hours with potassium succinimide (3.0 g). Water (300 ml) is added and the crude N-[2-oxo-2-spiro(cyclopentane-1,1'-indene)-3'-ylethyl]-imide is extracted with diethyl ether. The extract is carefully dried with sodium sulphate, concentrated to about 100 ml and added dropwise to a boiling solution of lithium aluminium hydride (5.0 g) in diethyl ether (250 ml) under nitrogen. The mixture is refluxed overnight and the excess of hydride is decomposed with a slight excess of saturated sodium sulphate solution. The inorganic salts are filtered off and washed with ether and the filtrate is dried. The solution is concentrated to about 200 ml and added to oxalic acid (2.0 g) in diethyl ether. The hydrogen oxalate precipitates and is recrystallized from a mixture of isopropyl alcohol/diisopropyl ether; m.p. 167° C.

EXAMPLE 6

3'-Spiro(cyclopentane-1,1'-indene)carbaldehyde

To 3'-bromospiro(cyclopentane-1,1'-indene) (7.5 g) in tetrahydrofuran, (500 ml) is added at −70° C. a solution of n-butyllithium in hexane (200 ml of a 1.8 M solution) in two portions. The temperature is kept at −70° C. for a further 30 minutes. Dimethylformamide (73 g) is then added and the mixture is allowed to come to about 20° C. After 3 hours sulphuric acid (400 ml; 1 M) and diethyl ether (200 ml) are added. The ether phase is separated, washed with saturated sodium chloride solution and dried over sodium sulphate. Evaporation of the ether and distillation gives the title aldehyde; b.p. 130°–135° C./0.1 torr.

In the same manner, the following compounds are prepared from the corresponding bromoindenes:
Spiro(cyclohexane-1,1'-indene)-3'-carbaldehyde; b.p. 125°–130° C./0.1 torr.
1,1-Dimethylindene-3-carbaldehyde; b.p. 82°–87° C./0.1 torr.

5'-Methoxyspiro(cyclopentane-1,1'-indene)-3'-carbaldehyde; b.p. 148°–150° C./0.1 torr.

Spiro(cyclopropane-1,1'-indene)-3'-carbaldehyde; solidifies after evaporation of the ether and is crystallized from cyclohexane without distillation; m.p. 112.5° C.

EXAMPLE 7

2-Amino-1-[5'-methoxyspiro(cyclopentane-1,1'-indene)-3'-yl]-ethanol

5'-Methoxyspiro(cyclopentane-1,1'-indene)-3'-carbaldehyde (4.4 g) is added to anhydrous aluminium chloride (0.1 g) in dichloromethane (25 ml). Trimethylsilyl cyanide (2.1 g) is added dropwise to the stirred mixture at about 20° C. and the mixture is stirred for 2 hours. The solvent is then removed under reduced pressure at about 25° C. bath temperature. The remaining oil is dissolved in anhydrous diethyl ether (50 ml) and slowly added to lithium aluminium hydride (3.5 g) in diethyl ether (200 ml). The mixture is stirred overnight and decomposed by careful addition of saturated, aqueous sodium sulphate solution (30 ml). The solid precipitate is removed by filtration and washed with diethyl ether. The combined filtrate and washings are concentrated to dryness and the solid is crystallized from diisopropyl ether; m.p. 118° C. The hydrogen fumarate is obtained from the base and an excess of fumaric acid in ethanol; m.p. 182° C.

In the same manner, the following compounds were prepared from the corresponding aldehydes:

2-Amino-1-[spiro(cyclohexane-1,1'-indene)-3'-yl]ethanol; m.p. 117° C. Hydrogen fumarate, m.p. 174° C.

2-Amino-1-(1,1-dimethylindene-3-yl)ethanol; m.p. 93° C. Neutral fumarate, m.p. 196° C.

2-Amino-1-[spiro(cyclopropane-1,1'-indene)-3'-yl]ethanol; m.p. 133°–134° C. Hydrochloride, m.p. 229° C.

2-Amino-1-[spiro(cyclopentane-1,1'-indene)-3'-yl]ethanol; m.p. 76°–78° C. Hydrochloride, m.p. 169°–172° C.

EXAMPLE 8

2-Methylamino-1-[spiro(cyclopentane-1,1'-indene)-3'-yl]ethanol

N-Methyl-[spiro(cyclopentane-1,1'-indan)-3'-yliden]acetamide (9.6 g; Swedish Pat. No. 7203905-0) is dissolved in dichloromethane (200 ml) and added to sodium bicarbonate solution (30 ml; 0.5 M). The solution is treated with m-chloroperbenzoic acid (13.76 g of a 50% product) in small portions with stirring at about 20° C. After stirring for an additional 2 hours, the solution is washed with saturated sodium carbonate solution and water and dried with sodium sulphate. The solvent is evaporated and the remaining oil is dissolved in tetrahydrofuran (100 ml). Perchloric acid (70%, 10 drops) is added and the mixture is kept at about 20° C. for 1.5 hour. Evaporation of the solvent in vacuo gives the crude α-hydroxy-N-methyl-[spiro(cyclopentane-1,1'-indene)-3'-yl]acetamide as a viscous oil. A sample is triturated with diisopropyl ether and the crystalline product obtained is recrystallized from this solvent. A colourless product is obtained, melting at 136°–138° C. The crude hydroxyamide is dissolved in anhydrous diethyl ether (200 ml) and added dropwise to a suspension of lithium aluminium hydride (30 g) in anhydrous ether (500 ml). The mixture is stirred at room temperature for 5 days and the excess of hydride is destroyed with ethyl acetate, followed by saturated aqueous sodium sulphate solution. The ether phase is washed with water and dried. Evaporation of the solvent gives the crude title compound, which after crystallization from diisopropyl ether melts at 134° C.

In an analogous manner, the following compounds are prepared from the corresponding acetamide derivatives:

2-Amino-1-[spiro(cyclopentane-1,1'-indene)-3'-yl]ethanol; m.p. 76°–78° C. (from cyclohexane).

2-Dimethylamino-1-[spiro(cyclopentane-1,1'-indene)-3'-yl]ethanol, oil. The hydrogen oxalate is prepared by adding an excess of oxalic acid, dissolved in acetonitrile, to the amine in acetonitrile, m.p. 133°–134° C.

2-Methylamino-1-[5'-chlorospiro(cyclopentane-1,1'-indene)-3'-yl]ethanol; m.p. 120° C.

2-Amino-1-(1,1-dimethylindene-3-yl)ethanol, oil. The fumarate, m.p. 196° C., is obtained from the base and fumaric acid in acetonitrile.

2-Amino-1-[spiro(cyclohexane-1,1'-indene)-3'-yl]ethanol, oil. The hydrogen fumarate is obtained from the amine and fumaric acid in ethanol; m.p. 174° C.

EXAMPLE 9

2-Methylamino-1-[spiro(cyclopentane-1,1'-indene)-3'-yl]ethanol

N-Methyl-2-[spiro(cyclopentane-1,1'-indene)-3'-yliden]ethylamine (8.1 g; Swedish Pat. No. 7203905-0) in diethyl ether (100 ml) is treated with trifluoroacetic anhydride (8 ml) while being stirred with powdered anhydrous sodium carbonate (6 g). The solid is filtered off and the solvent is evaporated from the filtrate. The crude N-trifluoroacetyl-N-methylspiro(cyclopentane-1,1'-indan)-3'-ylideneethylamine is dissolved in dichloromethane (100 ml), added to sodium bicarbonate solution (40 ml; 0.5 M) and treated in portions with m-chloroperbenzoic acid (50%; 3.4 g) with stirring at about 20° C. After stirring for 2 hours, the solution is washed with saturated sodium carbonate solution and water, and dried with sodium sulphate. After filtration, the solvent is evaporated. The crude epoxy compound is dissolved in tetrahydrofuran (100 ml), and treated with perchloric acid (10 drops) at room temperature for 2 hours. After evaporation of the solvent the remaining crude 2-(N-methyltrifluoroacetamido)-1-[spiro(cyclopentane-1,1'-indene)-3'-yl]-ethanol is dissolved in a mixture of methanol (20 ml), water (50 ml) and potassium carbonate (10 g) and stirred overnight. The methanol is evaporated under reduced pressure and the free amine is extracted into dichloromethane. After drying with sodium sulphate the solvent is evaporated. The title compound is crystallized from diisopropyl ether; m.p. 134° C.

In an analogous manner, the following compounds are prepared from the corresponding indanylidenethylamines:

2-Dimethylamino-1-[5'-chlorospiro(cyclopentane-1,1'-indene)-3'-yl]ethanol; m.p. 75° C.

2-Methylamino-1-(1,1-dimethylindene-3'-yl)ethanol; m.p. 120° C.

EXAMPLE 10

2-Dimethylamino-1-[spiro(cyclopentane-1,1'-indene)-3'-yl]-ethanol

(a)
N,N-Dimethyl-2-oxo-2-[spiro(cyclopentane-1,1'-indene)-3'-yl]acetamide

Butyllithium in hexane (13 ml of a 2 M solution) is added to 3'-bromospiro(cyclopentane-1,1'-indene) (5.0 g) in tetrahydrofuran at −70° C. After 10 minutes a solution of tetramethyloxyamide (5.8 g) in tetrahydrofuran (50 ml) is rapidly added. The mixture is stirred and allowed to come to about 20° C. After 2 hours, it is poured into a mixture of 50 ml 1 M hydrochloric acid and diethyl ether (100 ml) and the ether layer is separated. The aqueous phase is extracted twice with diethyl ether and the combined ether solutions are washed and dried. Evaporation of the solvent and crystallization from diisopropylether of the crude product obtained gives the colourless title compound; m.p. 119°–121° C.

(b)
2-Dimethylamino-1-[spiro(cyclopentane-1,1'-indene)-3'-yl]-ethanol

The oxoamide from step (a) (2.69) in anhydrous diethyl ether (200 ml) is stirred for 24 hours at about 20° C. with lithium aluminium hydride (2 g) in diethyl ether (100 ml). The excess of hydride is destroyed with saturated aqueous sodium sulphate solution. The ether phase is separated, washed, dried and concentrated to an oil which contains 2-dimethylamino-1-[spiro(cyclopentane-1,1'-indene)-3'-yl]ethanol contaminated by much of the corresponding indanyl analogue. The two compounds are separated by chromatography on aluminium oxide with diethyl ether/methanol as eluent. The product so obtained is converted into the hydrogen oxalate of the title compound in acetonitrile solution. M.p. 133°–134° C.

EXAMPLE 11

2-tert.-Butylamino-1-[spiro(cyclopentane-1,1'-indene)-3'-yl]ethanol

A solution of n-butyllithium in hexane (6 ml of a 2 M solution) is added dropwise under nitrogen to a stirred suspension of powdered trimethylsulphonium iodide in anhydrous tetrahydrofuran (30 ml) at 0° C. After stirring for 5 minutes, a solution of spiro(cyclopentane-1,1'-indene)-3'-carbaldehyde (2.0 g) in tetrahydrofuran (25 ml) is added. Stirring is continued at 0° C. for 1 hour, whereupon tert.-butylamine (1.0 g) is added and the mixture is allowed to come to about 20° C. After 24 hours, water (200 ml) is added and the solution is extracted three times with diethyl ether. The combined extracts are washed, dried and concentrated to about 50 ml. An excess of hydrogen chloride is added and the precipitated salt is collected and crystallized from ethanol; m.p. 292° C.

In an analogous manner, the following compounds are prepared from the corresponding aldehydes, amines and acids.

2-Methylamino-1-[spiro(cyclopentane-1,1'-indene)-3'-yl]-ethanol, hydrochloride; m.p. 217° C.
2-Amino-1-[spiro(cyclopropane-1,1'-indene)-3'-yl]ethanol, free base; m.p. 133°–134° C.
2-Dimethylamino-1-[spiro(cyclopentane-1,1'-indene)-3'-yl]ethanol, hydrogen oxalate; m.p. 134° C.
2-Amino-1-[spiro(cyclohexane-1,1'-indene)-3'-yl]ethanol, hydrogen fumarate; m.p. 117° C.

EXAMPLE 12

2-Isopropylamino-1-[spiro(cyclopentane-1,1'-indene)-3'-yl]ethanol

2-Amino-1-[spiro(cyclopentane-1,1'-indene)-3'-yl]ethanol (5.0 g) is refluxed with acetone (50 ml) for 12 hours and the excess of acetone is removed under reduced pressure. The crude N-isopropylidene derivative thus obtained is dissolved in diethyl ether (50 ml) and slowly added to a stirred mixture of lithium aluminium hydride (2.0 g) and diethyl ether (200 ml). After stirring for about 12 hours, the excess of hydride is decomposed with aqueous sodium sulphate solution. The ether phase is separated, dried with sodium sulphate and concentrated to give a viscous yellowish oil. This oil is dissolved in acetonitrile (100 ml) and added to a hot solution of oxalic acid (2.10 g) in 500 ml of acetonitrile. On cooling the solution forms colourless crystals of the hydrogen oxalate of the title compound. The crystals are collected and recrystallized from acetonitrile; m.p. 180° C.

EXAMPLE 13

2-Methylamino-1-[spiro(cyclopentane-1,1'-indene)-3'-yl-ethanol

Ethyl chloroformate (2.06 g) is added dropwise at about 7° C. to a stirred mixture of 2-amino-1-[spiro(cyclopentane-1,1'-indene)-3'-yl]ethanol (3.35 g) in chloroform (50 ml) and sodium hydroxide (0.9 g) in water (20 ml). After 2 hours, the chloroform phase is separated and the aqueous phase is extracted twice with chloroform. The combined chloroform solutions are dried and concentrated under reduced pressure. The crude 2-ethoxycarbonylamino-1-[spiro(cyclopentane-1,1'-indene)-3'-yl]ethanol thus obtained is dissolved in tetrahydrofuran (50 ml) and added dropwise to lithium aluminium hydride (1.8 g) in tetrahydrofuran (150 ml). After refluxing for 3 hours, the mixture is cooled and decomposed with a slight excess of saturated sodium sulphate solution. The solid precipitate is filtered off and washed with tetrahydrofuran. The combined filtrate and washings are dried and the solvent is removed, finally under reduced pressure. The residual oil crystallizes on scratching. Crystallization from diisopropyl ether gives the title compound; m.p. 134° C. 2-Ethylamino-1-[spiro(cyclopentane-1,1'-indene)-3'-yl]ethanol is similarly obtained when using acetic anhydride instead of ethyl chloroformate and reduction of the crude N-acetyl derivative. The free base is obtained as an oil, which is converted to the hydrochloride by treatment with hydrogen chloride in diethyl ether, m.p. 227° C. after crystallization from isopropyl alcohol. An identical product is obtained by reduction of crude 2-acetamido-1-[spiro(cyclopentane-1,1'-indene)-3'-yl]ethanol acetate obtained by the treatment of 2-amino-1-[spiro(cyclopentane-1,1'-indene)-3'-yl]ethanol with acetylchloride in diethyl ether containing an excess of triethylamine, removal of the precipitated triethylamine hydrochloride by filtration and evaporation of the filtrate.

EXAMPLE 14

2-Methylamino-1-[spiro(cyclopentane-1,1'-indene)-3'-yl]ethanol

Phosgene (1 g) is added to dimethylamino-1-[spiro(cyclopentane-1,1'-indene)-3'-yl]ethanol (2.9 g) in benzene (25 ml). The mixture is stirred at room temperature for 30 minutes and then under reflux for 2 hours. Evaporation of the solvent under reduced pressure gives an oil which crystallizes. Recrystallization from diisopropyl ether gives a pure product, m.p. 75°-77° C. This compound, 5-[spiro(cyclopentane-1,1'-indene)-3'-yl]ethanol (2 g), is refluxed for 2 hours with a solution of potassium hydroxide (5 g) in ethanol (50 ml) and water (10 ml). Most of the solvent is evaporated under reduced pressure, water (25 ml) is added and the amine is extracted into chloroform. Drying and evaporation of the solvent gives the crystalline title compound, which after recrystallization from diisopropyl ether melts at 133°-134° C.

EXAMPLE 15

2-Dimethylamino-1-[spiro(cyclopentane-1,1'-indene)-3'-yl]ethanol

Ethyl chloroformate (0.7 g) and sodium hydroxide (0.3 g) dissolved in water (10 ml) are added to 2-methylamino-1-[spiro(cyclopentane-1,1'-indene)-3'-yl]ethanol (1.3 g) in chloroform (25 ml). The mixture is stirred vigorously for 2 hours at about 10° C. The chloroform layer is separated, washed with water and dried. The solvent is removed in vacuo and the residual crude 2-(N-ethoxycarbonyl-N-methylamino)-1-[spiro(cyclopentane-1,1'-indene)-3'-yl]ethanol is dissolved in tetrahydrofuran (75 ml) and added to lithium aluminium hydride (2.0 g) in tetrahydrofuran (25 ml). The mixture is refluxed for 3 hours, and the excess of hydride is destroyed with a slight excess of saturated aqueous sodium sulphate solution. The inorganic salt precipitate is filtered off and washed with tetrahydrofuran. The combined filtrate and washings are dried over sodium sulphate and the solvent is removed under reduced pressure. The crude title compound is dissolved in acetonitrile and treated with a slight excess of oxalic acid dissolved in acetonitrile. The slowly depositing hydrogen oxalate is collected by filtration and recrystallization from acetonitrile; m.p. 133°-134° C.

EXAMPLE 16

2-Trimethylammonio-1-[spiro(cyclopentane-1,1'-indene)-3'-yl]ethanol

Methyl iodide (8 g) is added to 2-dimethylamino-1-[spiro(cyclopentane-1,1'-indene)-3'-yl]ethanol (1.3 g) in diethyl ether (100 ml). The mixture is kept for 24 hours and the precipitated methiodide is collected by filtration; m.p. 115°-120° C. (decomposition).

EXAMPLE 17

2-Dimethylamino-1-[spiro(cyclopentane-1,1'-indene)-3'-yl]ethanol-N-oxide

2-Dimethylamino-1-[spiro(cyclopentane-1,1'-indene)-3'-yl]ethanol (5.4 g), hydrogen peroxide (2.3 g, 30%) and methanol (10 ml) are mixed and kept for 2 days at about 20° C. The solution is evaporated to dryness and the solid is dried in vacuo over phosphorous pentoxide to remove water. After crystallization from anhydrous acetone/diisopropyl ether the crystals of the title compound melted at 151° C.

EXAMPLE 18

Resolution of 2-methylamino-1-[spiro(cyclopentane-1,1'-indene)-3'-yl]ethanol (±)-2-Methylamino-1-[spiro(cyclopentane-1,1'-indene)-3'-yl]ethanol (12 g) is dissolved in ethanol (75 ml) and added to a solution of D(−)-tartaric acid (15 g) in water (300 ml) at about 20° C. The mixture is concentrated at reduced pressure to 200 ml and kept overnight at 4° C. The crystalline precipitate is collected and recrystallised from water until constant specific rotation is obtained, which requires 3 to 5 recrystallizations. The (−)-2-methylamino-1-[spiro(cyclopentane-1,1'-indene)-3'-yl]ethanol (−)-hydrogen tartrate melts at 79°-83° C.; $[\alpha]_{546}^{20} = -32.6°$ (c=1 in water).

The original mother liquor and the liquors from the first two recrystallizations are combined and made alkaline with 2 N sodium hydroxide solution. The free base is extracted into dichloromethane, and the extract is washed and dried. After evaporation of the solvent the crude base in ethanol (300 ml) is treated with L(+)-tartaric acid (5.6 g) in water (300 ml) as described above for the preparation of the (−)salt. The (+)-2-methylamino-1-[spiro(cyclopentane-1,1'-indene)-3'yl]ethanol (+)-hydrogen tartrate melts at 85°-90° C.; $[\alpha]_{546}^{20} = +34.4°$ (c=1 in water).

The pharmacological properties of the various compounds of the invention were demonstrated by the following test procedure.

Effect on Rat Isolated Vas Deferens

Male albino rats weighing 250-350 g were anaesthetized with diethyl ether and then decapitated. The vas deferens was removed, freed from mesenteric attachments and then suspended in Kreb's bicarbonate solution (Hukovic, 1961). Threads were attached to both ends of the organ. The distal part was tied to a fixed pin in the organ bath and the proximal part to a force displacement transducer connected to a recording system. The organ bath had a volume of 10 ml and was surrounded by a waterjacket of 31° C., and the bath was gassed with 93.5% $O_2$ and 6.5% $CO_2$. The load on the organ was adjusted to 0.5 g. The vas deferens was allowed to stabilize for 15 minutes before dose-response curves were obtained.

The technique for making cumulative dose-response curves in accordance with van Rossum (1963) was employed. The stimulating drug, noradrenaline (NA), was added to the bath in a manner to achieve geometrically increasing concentrations in the organ bath without washings in between. After each injection of NA the organ was allowed to contract until a state of equilibrium had been reached, and then the next dose of NA was added. This procedure was repeated until no further increase in contraction was obtained. The dosage of NA was adapted to give a concentration step in the bath of ½ log 10. The tested concentration interval was $10^{-8}$–$10^{-4}$ M, $3.10^{-4}$ M plus maximum effect at $3 \cdot 10^{-5}$ and $10^{-4}$ M. Compounds of formula I, identified as 2-12, and comparison compounds 13-15, were tested by the same technique. The compounds conform to the formula below except where indicated for other values of $R^1$, $R^2$ and $R^3$. The test results are given in Table 1 below.

Table 1

Structure:

[spiro indene structure with R substituent]

| Substance, R | threshold conc., M | $EC_{50}$, M |
|---|---|---|
| 1. noradrenaline | $10^{-6}$ | $3 \cdot 10^{-5}$ |
| 2. —CH(OH)—CH$_2$NH$_2$ | $10^{-7}$ | $4 \cdot 10^{-5}$ |
| 3. —CH(OH)—CH$_2$NHCH$_3$ | $3 \cdot 10^{-8}$ | $1.5 \cdot 10^{-7}$ |
| 4. —CH(OH)—CH$_2$NHC$_2$H$_5$ | $5 \cdot 10^{-7}$ | $1.5 \cdot 10^{-6}$ |
| 5. —CH(OH)—CH$_2$N(CH$_3$)$_2$ | $10^{-5} - 10^{-4}$ | — |

| Substance, R | threshold cont., M | $EC_{50}$, M |
|---|---|---|
| 6. —CH(OH)—CH$_2$NHCH(CH$_3$)$_2$ | $10^{-6}$ / $3 \cdot 10^{-6}$ | $4 \cdot 10^{-6}$ |
| 7. —CH(OH)—CH$_2$NH$_2$; R$^1$,R$^2$ = —CH$_2$— | $10^{-6}$ / $3 \cdot 10^{-6}$ | $1.5 \cdot 10^{-5}$ |
| 8. —CH(OH)—CH$_2$NH$_2$; R$^1$ = R$^2$ = H | $3 \cdot 10^{-7}$ | $2 \cdot 10^{-6}$ |
| 9. —CH(OH)—CH$_2$NH$_2$; R$^1$,R$^2$ = —(CH$_2$)$_3$— | $3 \cdot 10^{-6}$ | $1.5 \cdot 10^{-5}$ |
| 10. —CH(OH)—CH$_2$NH$_2$; R$^3$ = CH$_3$O— in position 5 | $5 \cdot 10^{-6}$ | $5 \cdot 10^{-5}$ |
| 11. (−)-form of No. 3 | $3 \cdot 10^{-8}$ | $7 \cdot 10^{-8}$ |
| 12. (+)-form of No. 3 | $5 \cdot 10^{-6}$ | — |
| 13. —C(=O)—CH$_2$N(CH$_3$)$_2$ | — | — |
| 14. No. 3 without double bond | — | — |
| 15. —CH$_2$CH$_2$NH(CH$_3$) | — | — |

| Substance, R | max. effect, % of NA max. | n |
|---|---|---|
| 1. noradrenaline | 100 | 10 |
| 2. —CH(OH)—CH$_2$NH$_2$ | 100 | 7 |
| 3. —CH(OH)—CH$_2$NHCH$_3$ | 100 | 10 |
| 4. —CH(OH)—CH$_2$NHC$_2$H$_5$ | 85 | 2 |
| 5. —CH(OH)—CH$_2$N(CH$_3$)$_2$ | 50 | 2 |
| 6. —CH(OH)—CH$_2$NHCH(CH$_3$)$_2$ | 90 | 2 |
| 7. —CH(OH)—CH$_2$NH$_2$; R$^1$,R$^2$ = —CH$_2$— | 120 | 2 |
| 8. —CH(OH)—CH$_2$NH$_2$; R$^1$ = R$^2$ = H | 100 | 2 |
| 9. —CH(OH)—CH$_2$NH$_2$; R$^1$,R$^2$ = —(CH$_2$)$_3$— | 70 | 2 |
| 10. —CH(OH)—CH$_2$NH$_2$; R$^3$ = CH$_3$O— in position 5 | 65 | 2 |
| 11. (−)-form of No. 3 | 90 | 2 |
| 12. (+)-form of No. 3 | 35 | 2 |
| 13. —C(=O)—CH$_2$N(CH$_3$)$_2$ | 0 | 2 |
| 14. No. 3 without double bond | 0 | 3 |
| 15. —CH$_2$CH$_2$NH(CH$_3$) | 0 | — |

As appears from the above test results, the effect is highly structure-specific. Thus, the corresponding ketone is inactive; see comparison compound No. 13. Furthermore, the effect disappears when the indene double bond is hydrogenated (see comparison compound No. 14) or when the hydroxyl group is removed (see comparison compound No. 15).

Effect on urethra strip of cat and aortic strip of rabbit

Adult male and female cats weighing 2–5 kg were used. The animals were anaesthetized with pentobarbital, 30–50 mg/kg intraperitoneally. An abdominal incision was made and the bladder and urethra were dissected free and cut. The bladder and urethra were placed in Tyrode solution of room temperature. Care was taken to keep the tissue moist during the preparation. The bladder was cut away and the urethra was cut longitudinally. Segments of 2–3 mm width were mounted in an organ-bath with Tyrode solution at 37° C. and connected to a strain gauge transducer so that the isometric tension could be recorded. The preparation was maintained at pH 7.5 by bubbling a mixture of 93.5 volume-% $O_2$ and 6.5 volume-% $CO_2$ through the solution. This experimental set up thus allowed the recording of circular muscle activity as isometric tension changes. The initial tension was set at approximately 0.5 g. After mounting, the preparation was allowed 1 hour for acclimatization before starting the experiment. All recordings were made from the base line. The drugs were added directly to the organ-baths and cumulative dose-response curves were recorded. Noradrenaline has consistently been used as a reference drug for agonistic action. The substances tested as agonists were noradrenaline bitartrate (NA) and the above compound No. 3. The test results are reported in Table 2 below, which also indicates the results of corresponding tests on aortic strips of rabbit in order to illustrate the selective effect on urethra of the compound according to the invention.

Table 2

| | $EC_{50}$-values | | index |
|---|---|---|---|
| | compound No. 3 | NA | No. 3/NA |
| Urethra strip (cat) | $(6.9 \pm 3.6) \cdot 10^{-7}$M | $(2.7 \pm 0.4) \cdot 10^{-5}$M | ~40 |
| Aortic strip (rabbit) | $(4.5 \pm 1.4) \cdot 10^{-8}$M | $(1.8 \pm 0.8) \cdot 10^{-7}$M | ~4 |

We claim:

1. Geminally disubstituted indenes characterised in that they are of the formula (I)

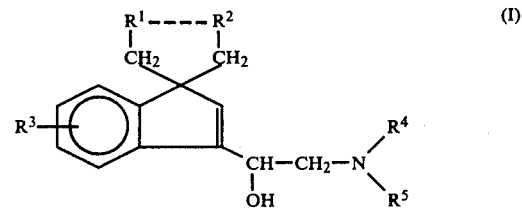

wherein each of R$^1$ and R$^2$ is hydrogen or R$^1$ and R$^2$ together form a direct bond or an alkylene group —(CH$_2$)$_n$—, in which n is an integer from 1 to 4, R$^3$ is hydrogen, C$_{1-3}$-alkoxy or halogen, and each of R$^4$ and R$^5$ is hydrogen or C$_{1-4}$-lower alkyl, or R$^4$ and R$^5$ together form an alkylene group —(CH$_2$)—, in which m is an integer from 3 to 6; and salts with physiologically acceptable acids thereof.

2. An indene according to claim 1 wherein R$^1$ and R$^2$ together represent —CH$_2$—CH$_2$— or —CH$_2$— or each represent H.

3. An indene according to claim 1 or 2 wherein $R^4$ is H and $R^5$ is H or $CH_3$.

4. An indene according to claim 1 wherein $R^3$ is H.

5. An indene according to claim 1 which is 2-amino-1-[spiro(cyclopentane-1,1'-indene)-3'-yl]-ethanol; 2-methylamino-1-[spiro(cyclopentane-1,1'-indene)-3'-yl]-ethanol; 2-amino-1-[spiro-(cyclopentane-1,1'-indene)-3'-yl]-ethanol or 2-amino-1-[1,1-dimethylindene-3-yl]-ethanol.

6. An indene according to claim 1 or 2 or 5 in the form of a hydrochloride, hydrogen fumarate, hydrogen oxalate or hydrogen tartrate.

7. An indene according to claim 1 or 2 or 5 in the form on an optically active isomer.

8. An indene according to claim 3 wherein $R^3$ is H.

9. An indene according to claim 3 in the form of a hydrochloride, hydrogen fumarate, hydrogen oxalate or hydrogen tartrate.

10. An indene according to claim 4 in the form of a hydrochloride, hydrogen fumarate, hydrogen oxalate or hydrogen tartrate.

11. An indene according to claim 3 in the form of an optically active isomer.

12. An indene according to claim 4 in the form of an optically active isomer.

13. An indene according to claim 6 in the form of an optically active isomer.

14. A pharmaceutical composition comprising an indene or salt thereof according to claim 1 or 2 or 5 in an amount effective for providing a sympathomimetic amount in association with a pharmaceutically acceptable carrier.

15. The pharmaceutical composition of claim 14 wherein $R^4$ is H and $R^5$ is H or $CH_3$.

16. The pharmaceutical composition of claim 15 wherein $R^3$ is H.

17. The pharmaceutical composition of claim 14 wherein $R^3$ is H.

18. The pharmaceutical composition of claim 14 wherein said indene is in the form of a hydrochloride, hydrogen fumarate, hydrogen oxalate or hydrogen tartrate.

19. The pharmaceutical composition of claim 15 wherein said indene is in the form of a hydrochloride, hydrogen fumarate, hydrogen oxalate or hydrogen tartrate.

20. The pharmaceutical composition of claim 16 wherein said indene is in the form of a hydrochloride, hydrogen fumarate, hydrogen oxalate or hydrogen tartrate.

21. The pharmaceutical composition of claim 17 wherein said indene is in the form of a hydrochloride, hydrogen fumarate, hydrogen oxalate or hydrogen tartrate.

22. The pharmaceutical composition of claim 14 wherein said indene or salt thereof is in the form of an optically active isomer.

23. The pharmaceutical composition of claim 15 wherein said indene or salt thereof is in the form of an optically active isomer.

24. The pharmaceutical composition of claim 16 wherein said indene or salt thereof is in the form of an optically active isomer.

25. The pharmaceutical composition of claim 12 wherein said indene or salt thereof is in the form of an optically active isomer.

26. The pharmaceutical composition of claim 18 wherein said indene or salt thereof in in the form of an optically active isomer.

27. A method of treatment involving a sympathomimetic effect which comprises administering to a host in need of such treatment an effective amount for such treatment of a compound, or salt thereof, or optically active isomer thereof according to claim 1 or 2 or 5.

28. The method of claim 27 wherein $R^4$ is H and $R^5$ is H or $CH_3$.

29. The method of claim 28 wherein $R^3$ is H.

30. The method of claim 27 wherein $R^3$ is H.

31. The method of claim 27 wherein said indene is in the form of a hydrochloride, hydrogen fumarate, hydrogen oxalate or hydrogen tartrate.

32. The method of claim 28 wherein said indene is in the form of a hydrochloride, hydrogen fumarate, hydrogen oxalate or hydrogen tartrate.

33. The method of claim 29 wherein said indene is in the form of a hydrochloride, hydrogen fumarate, hydrogen oxalate or hydrogen tartrate.

34. The method of claim 30 wherein said indene is in the form of a hydrochloride, hydrogen fumarate, hydrogen oxalate or hydrogen tartrate.

35. The method of claim 27 wherein indene or salt thereof is in the form of an optically active isomer.

36. The method of claim 28 wherein indene or salt thereof is in the form of an optically active isomer.

37. The method of claim 29 wherein indene or salt thereof is in the form of an optically active isomer.

38. The method of claim 30 wherein indene or salt thereof is in the form of an optically active isomer.

* * * * *